US010959794B2

(12) United States Patent
Peine

(10) Patent No.: US 10,959,794 B2
(45) Date of Patent: *Mar. 30, 2021

(54) ROBOTICALLY CONTROLLING REMOTE CENTER OF MOTION WITH SOFTWARE AND GUIDE TUBE

(71) Applicant: Covidien LP, Mansfield, MA (US)

(72) Inventor: William Peine, Ashland, MA (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/717,482

(22) Filed: Dec. 17, 2019

(65) Prior Publication Data
US 2020/0121405 A1    Apr. 23, 2020

Related U.S. Application Data

(63) Continuation of application No. 15/548,473, filed as application No. PCT/US2016/014219 on Jan. 21, 2016, now Pat. No. 10,517,684.
(Continued)

(51) Int. Cl.
*A61B 34/00* (2016.01)
*A61B 34/35* (2016.01)
(Continued)

(52) U.S. Cl.
CPC .......... *A61B 34/35* (2016.02); *A61B 17/3421* (2013.01); *A61B 34/30* (2016.02);
(Continued)

(58) Field of Classification Search
USPC ................................................ 700/245–264
See application file for complete search history.

(56) References Cited

U.S. PATENT DOCUMENTS 5,397,323 A * 3/1995 Taylor .................. B25J 19/0008
606/130
5,800,423 A * 9/1998 Jensen ................... B25J 9/1065
606/1
(Continued)

FOREIGN PATENT DOCUMENTS

JP    2014223552 A    12/2014
WO   2007142698 A2   12/2007
(Continued)

OTHER PUBLICATIONS

Chinese Office Action issued in corresponding Chinese Application No. 201680012409.2 dated Mar. 3, 2020, 13 pages.
(Continued)

*Primary Examiner* — Jonathan L Sample
(74) *Attorney, Agent, or Firm* — Carter, DeLuca & Farrell LLP

(57) ABSTRACT

A robotic surgical system includes a surgical robot and a guide tube. The surgical robot includes a robot arm and a controller. The controller is configured to establish a software-based remote center of motion of a surgical instrument attached to the robot arm based on a location of a surgical portal in a patient through which the surgical instrument is inserted. The guide tube having a trailing end supported by the robot arm of the surgical robot, a leading end inserted in the surgical portal and maintaining alignment between the robotic arm and the surgical portal during a surgical instrument exchange, and an elongated tubular body through which an elongated shaft of the surgical instrument is inserted or removed during the surgical instrument exchange.

20 Claims, 7 Drawing Sheets

Related U.S. Application Data

(60) Provisional application No. 62/121,283, filed on Feb. 26, 2015.

(51) Int. Cl.
  *A61B 34/30* (2016.01)
  *A61B 17/34* (2006.01)
  *A61B 46/10* (2016.01)
  *A61B 90/50* (2016.01)

(52) U.S. Cl.
  CPC .............. *A61B 46/10* (2016.02); *A61B 17/34* (2013.01); *A61B 17/3403* (2013.01); *A61B 17/3462* (2013.01); *A61B 90/50* (2016.02); *A61B 2034/301* (2016.02); *A61B 2034/302* (2016.02); *A61B 2034/305* (2016.02)

(56) References Cited

U.S. PATENT DOCUMENTS

| | | | |
|---|---|---|---|
| 6,699,177 B1 | 3/2004 | Wang et al. | |
| 8,004,229 B2 * | 8/2011 | Nowlin | A61B 34/35 318/568.21 |
| 8,303,576 B2 * | 11/2012 | Brock | A61B 34/71 606/1 |
| 10,517,684 B2 | 12/2019 | Peine | |
| 2006/0161138 A1 * | 7/2006 | Orban, III | A61B 34/35 606/1 |
| 2008/0064921 A1 * | 3/2008 | Larkin | A61B 1/018 600/104 |
| 2008/0065111 A1 * | 3/2008 | Blumenkranz | A61B 34/37 606/130 |
| 2009/0024142 A1 * | 1/2009 | Ruiz Morales | A61B 34/35 606/130 |
| 2009/0234369 A1 * | 9/2009 | Bax | A61B 17/3403 606/130 |
| 2010/0204713 A1 * | 8/2010 | Ruiz Morales | A61B 34/37 606/130 |
| 2010/0274087 A1 * | 10/2010 | Diolaiti | A61B 1/00087 600/118 |
| 2011/0071508 A1 * | 3/2011 | Duval | A61B 1/00183 606/1 |
| 2011/0277580 A1 * | 11/2011 | Cooper | A61B 34/71 74/490.04 |
| 2011/0277775 A1 * | 11/2011 | Holop | A61B 46/23 128/849 |
| 2011/0282351 A1 * | 11/2011 | Cooper | A61B 34/00 606/108 |
| 2012/0116416 A1 | 5/2012 | Neff et al. | |
| 2012/0245596 A1 | 9/2012 | Meenink | |
| 2013/0165948 A1 * | 6/2013 | Popovic | A61B 1/00149 606/130 |
| 2013/0304084 A1 * | 11/2013 | Beira | A61B 34/71 606/130 |
| 2014/0005684 A1 * | 1/2014 | Kim | A61B 34/30 606/130 |
| 2014/0039314 A1 * | 2/2014 | Stoianovici | A61B 34/30 600/439 |
| 2014/0066717 A1 | 3/2014 | Rogers et al. | |
| 2014/0236175 A1 * | 8/2014 | Cooper | A61B 34/74 606/130 |
| 2014/0243850 A1 * | 8/2014 | Sadaka | A61B 34/30 606/130 |
| 2016/0184037 A1 * | 6/2016 | Cooper | A61B 34/30 606/130 |
| 2016/0235486 A1 * | 8/2016 | Larkin | A61B 1/00154 |
| 2018/0042686 A1 * | 2/2018 | Peine | A61B 34/30 |

FOREIGN PATENT DOCUMENTS

| | | |
|---|---|---|
| WO | 2013075205 A1 | 5/2013 |
| WO | 2014020571 A1 | 2/2014 |
| WO | 2014144233 A1 | 9/2014 |
| WO | 2014155257 A1 | 10/2014 |
| WO | 2015088647 A1 | 6/2015 |

OTHER PUBLICATIONS

International Search Report and Written Opinion issued in corresponding International Application PCT/US2016/014219 dated May 13, 2016, 8 pages.
European Search Report issued in European Application No. 16756012.7 dated Sep. 28, 2018.
Chinese Office Action issued in corresponding Chinese Application No. 2016800124092 dated Aug. 16, 2019, 16 pages.
Japanese Office Action issued in corresponding Japanese Application No. 2017-543780 dated Sep. 27, 2019, 12 pages.
Japanese Office Action issued in corresponding Japanese Application No. 201680012409.2 dated Mar. 3, 2020, 13 pages.
EP Office Action for Application No. 16 756 012.7 dated Sep. 28, 2020.
Chinese Office Action for Application No. 2016800124092 dated Aug. 4, 2020 with English translation.
India Examination Report for application No. 201717027697 dated Nov. 18, 2020.

\* cited by examiner

ROBOTICALLY CONTROLLING REMOTE CENTER OF MOTION WITH SOFTWARE AND GUIDE TUBE

CROSS-REFERENCE TO RELATED APPLICATION

This application is a continuation of U.S. patent application Ser. No. 15/548,473, filed Aug. 3, 2017, which is a U.S. National Stage Application filed under 35 U.S.C. § 371(a) of International Patent Application Serial No. PCT/US2016/014219, filed Jan. 21, 2016, which claims the benefit of U.S. Provisional Patent Application No. 62/121,283, filed on Feb. 26, 2015, the entire contents of which is incorporated by reference herein.

BACKGROUND

Robotic surgical systems have been used in minimally invasive medical procedures in which surgical instruments were inserted through surgical portals at fixed entry points into the patient's body. These systems incorporated a Remote Center of Motion (RCM) to ensure that the surgical instruments did not move beyond these fixed entry points as the instruments were manipulated inside the patient's body. Many of these surgical robots used a mechanical RCM with a portion of robotic arm attaching directly to the surgical portal. Unlike surgical robots using mechanical RCM's, software-based RCM's typically did not mechanically connect to the surgical portal in order to provide an increased range of motion and reduce collisions between robotic arms of the surgical robot. Unfortunately, many of the surgical robots with software-based RCM's tend to complicate instrument exchanges as the surgical portals moved out of alignment with the robotic arms when the surgical instruments were removed.

During an instrument exchange, the surgical instrument was pulled out of the surgical port and removed from the robotic arm. A new or different surgical instrument was then connected to the robotic arm and introduced back through the surgical portal. Surgical robots with mechanical based RCM's facilitated the exchange because the surgical portal was continually held in alignment with the linear axis of the instrument motion by a linkage or connection to the surgical portal. In contrast, surgical robots with software-based RCM's did not have a connection or linkage to the surgical portal and therefore lost alignment when the surgical instrument was removed from the surgical portal. Inserting another surgical instrument required the clinician to manually align the surgical portal with the surgical instrument. This process increased the time required for conducting the instrument exchange.

Accordingly, there is a need for robotic surgical systems with software-based RCM's that facilitate instrument exchange by maintaining alignment of the surgical portal and robotic arm.

SUMMARY

The present disclosure is directed to a guide tube that speeds up the instrument exchange process and eliminates the need for a clinician to hold the surgical portal during an insertion of the surgical instrument into the surgical portal.

The described guide tube can cover an entire instrument shaft of the surgical instrument with only the distal wrist assembly thereof exposed at a surgical site so that a distal end of the guide tube remains in a field of view of an in vivo endoscope while the surgical instrument is removed. Thus, with the benefit of the guide tube, a final, exact in vivo location of the end effector of the new or different instrument will be known by the clinician prior to reinsertion. Knowing this final location of the end effector in vivo advantageously increases safety of the instrument exchange. Safety is further increased because the guide tube provides a barricaded conduit for the surgical instrument all the way to the surgical site visible by the endoscopic camera. Ideally, under normal circumstance of an instrument exchange, the clinician should always move or adjust the endoscope away from the surgical site to view the surgical portal during the instrument exchange to ensure that the surgical instrument does not catch or puncture organs/connective tissues while the new or different surgical instrument is inserted. The presently described guide tube eliminates the need to make such movement or adjustment of the endoscope. Further, the guide tube provides mechanical reinforcement to the instrument shaft of the surgical instrument to reduce bending and can be connected to ground to provide electrical isolation for improving safety while using electrosurgery.

In one aspect, a robotic surgical system includes a surgical robot and a guide tube.

The surgical robot includes a robot arm and a controller. The controller is configured to establish a software-based remote center of motion of a surgical instrument attached to the robot arm based on a location of a surgical portal in a patient through which the surgical instrument is inserted.

The guide tube has a trailing end supported by the robot arm of the surgical robot, a leading end inserted in the surgical portal and maintaining alignment between the robotic arm and the surgical portal during a surgical instrument exchange, and an elongated tubular body through which an elongated shaft of the surgical instrument is inserted or removed during the surgical instrument exchange. The guide tube is slidably movable relative to surgical portal in response to movement of the robotic arm.

The guide tube and the robotic arm define a first longitudinal axis that extends between the leading and trailing ends of the guide tube. The surgical portal defines a second longitudinal axis that extends between the leading and trailing ends thereof. The first longitudinal axis is configured to maintain coaxial alignment with the second longitudinal axis during the surgical instrument exchange.

In embodiments, guide tube includes an internal seal configured to maintain a sealed relationship with surgical instruments received within the guide tube. The guide tube may be formed of an electrically conductive material. The guide tube can be grounded.

The robotic surgical system may further include a sterile drape positioned between the guide tube and the robotic arm.

According to another aspect, a method comprises setting a software-based remote center of motion (RCM) of a robot arm of a surgical robot after the robot arm is moved into a position in which a leading end of a guide tube supported by the robot arm is inserted in a surgical portal in a patient. Setting the software-based RCM may include storing a location of the surgical portal. The guide tube has an elongated tubular body through which an elongated shaft of the surgical instrument passes through as a surgical instrument controlled by the robot arm is inserted in or removed from the surgical portal.

The method involves robotically moving the robot arm and the surgical instrument about the set software-based RCM and maintaining an alignment between the robotic arm and the surgical portal during a surgical instrument exchange when the surgical instrument is not in the surgical portal.

Robotically moving the robot arm and the surgical instrument about a set software-based RCM may include sliding the guide tube relative to the surgical portal.

The method may include electrically communicating the location of the surgical portal to the robotic arm.

The method may further include advancing an endoscope through a second surgical portal adjacent to the surgical portal, and positioning the endoscope to maintain a leading end of the guide tube within a field of view of the endoscope. The method may involve maintaining the leading end of the guide tube within the field of view of the endoscope during the surgical instrument exchange.

Further details and aspects of exemplary embodiments of the present disclosure are described in more detail below with reference to the appended figures.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
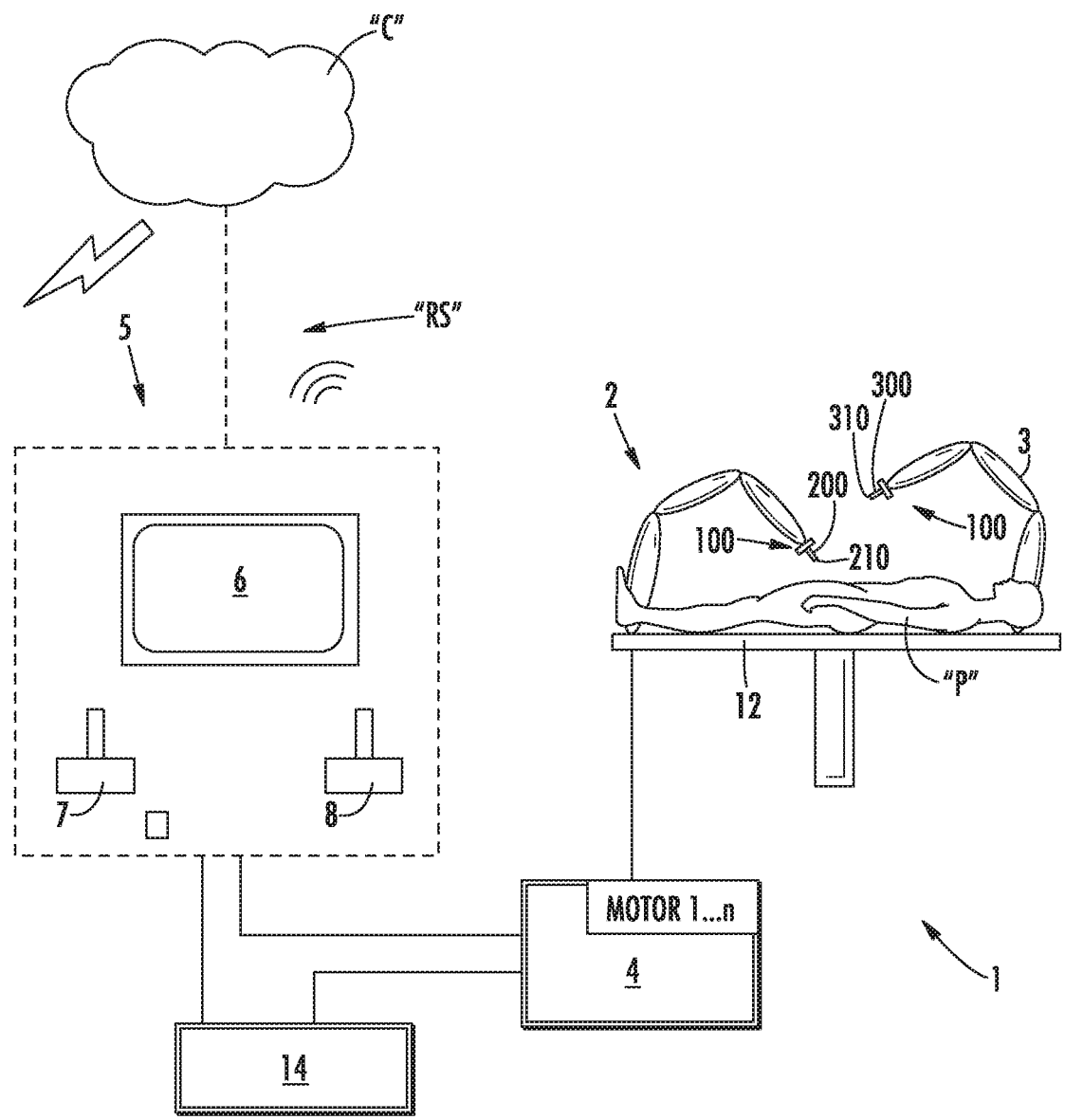
FIG. 1 is a schematic illustration of a robotic surgical system in accordance with the present disclosure.

Embodiments of the present disclosure are described in detail with reference to the drawings, in which like reference numerals designate identical or corresponding elements in each of the several views. As used herein, the term "distal" refers to that portion of a device that is farther from the user, while the term "proximal" refers to that portion of a device that is closer to the user.

Referring initially to FIG. 1, a surgical system, such as, for example, a robotic surgical system is shown generally as robotic surgical system 1 and generally includes a plurality of robotic arms 2, 3; a controller or control device 4; and an operating console 5 coupled with control device 4. Operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art.

Robotic surgical system 1 also includes a surgical assembly 100 connected to a distal end of each of robotic arms 2, 3. Surgical assembly 100 may support one or more surgical instruments such as surgical instruments 200, 300, as will be described in greater detail below.

Figure 2:
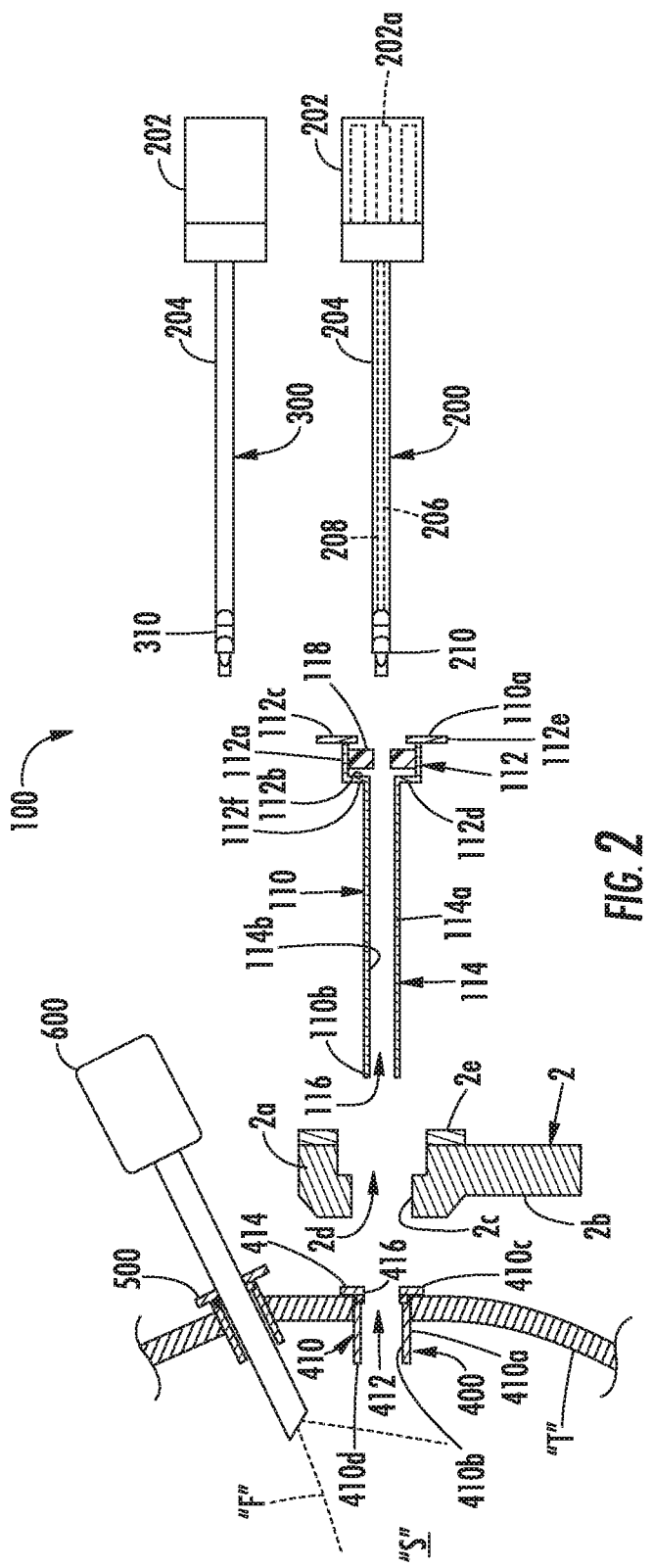
FIG. 2 is an enlarged elevational view, with parts separated, of a surgical assembly of the robotic surgical system of FIG. 1.

Each of the robotic arms 2, 3 is composed of a plurality of members, which are connected through joints. Referring also to FIG. 2, robotic arm 2 (and/or robotic arm 3) includes a mounting portion 2a having an outer surface 2b and an inner surface 2c. Inner surface 2c defines a receiving passage 2d therethrough and outer surface 2b that may support a sterile drape 2e thereon. Sterile drape 2e can be disposable and/or replaceable. Inner surface 2c may form a shoulder 2g that functions to support one of surgical instruments 200, 300.

Robotic arms 2, 3 may be driven by electric drives (not shown) that are connected to control device 4. Control device 4 (e.g., a computer) is set up to activate the drives, in particular by means of a computer program, in such a way that robotic arms 2, 3, their surgical assemblies 100 and/or surgical instruments 200, 300 execute a desired movement according to a movement defined by means of manual input devices 7, 8. Control device 4 may also be set up in such a way that it regulates movement of robotic arms 2, 3 and/or of the drives. While electrically coupled to controller or control device 4, as described above, robotic arms 2, 3 are configured to receive signals from controller 4, which may be software-based, to establish a remote center of motion at any suitable location as described in greater detail below.

Robotic surgical system 1 is configured for use on a patient "P" lying on a patient table 12 to be treated in a minimally invasive manner by means of an end effector of one or more of the surgical instruments. Surgical system 1 may also include more than two robotic arms 2, 3, the additional robotic arms likewise being connected to control device 4 and being telemanipulatable by means of operating console 5. One or more additional surgical assemblies 100 and/or surgical instruments 200, 300 may also be attached to the additional robotic arm.

Control device 4 may control a plurality of motors (Motor 1 . . . n) with each motor configured to drive a pushing or a pulling of one or more cables of surgical instruments 200, 300. As described below, the plurality of motors can include a plurality of motors 202a of an instrument drive unit 202 of surgical instruments 200, 300 as shown in FIG. 2. In use, as these cables are pushed and/or pulled, the one or more cables effect operation and/or movement of end effectors 210, 310 of surgical instruments 200, 300. It is contemplated that control device 4 coordinates the activation of the various motors (Motor 1 . . . n) to coordinate a pushing or a pulling motion of these cables in order to coordinate an operation and/or movement of end effectors 210, 310. Reference may be made to International Application No. PCT/US2014/61329, filed on Oct. 20, 2014, entitled "Wrist and Jaw Assemblies for Robotic Surgical Systems," the entire content of which is incorporated herein by reference, for a detailed discussion of the construction and operation of end effectors 210, 310.

In embodiments, each motor can be configured to actuate a drive rod or a lever arm to effect operation and/or movement of end effectors 210, 310 in addition to, or instead of one or more cables.

Control device 4 can include any suitable logic control circuit adapted to perform calculations and/or operate according to a set of instructions. Control device 4 can be configured to communicate with a remote system "RS," either via a wireless (e.g., Wi-Fi, Bluetooth, LTE, etc.) and/or wired connection. Remote system "RS" can include data, instructions and/or information related to the various components, algorithms, and/or operations of work station 1. Remote system "RS" can include any suitable electronic service, database, platform, cloud "C," or the like. Control device 4 may include a central processing unit operably connected to memory. The memory may include transitory type memory (e.g., RAM) and/or non-transitory type memory (e.g., flash media, disk media, etc.). In some embodiments, the memory is part of, and/or operably coupled to, remote system "RS."

Control device 4 can include a plurality of inputs and outputs for interfacing with the components of robotic surgical system 1, such as through a driver circuit. Control device 4 can be configured to receive input signals and/or generate output signals to control one or more of the various components (e.g., one or more motors) of robotic surgical system 1. The output signals can include, and/or can be based upon, algorithmic instructions which may be pre-programmed and/or input by a user. Control device 4 can be configured to accept a plurality of user inputs from a user interface (e.g., switches, buttons, touch screen, etc. of operating console 5) which may be coupled to remote system "RS."

A database 14 can be directly and/or indirectly coupled to control device 4. Database 14 can be configured to store pre-operative data from living being(s) and/or anatomical atlas(es). Database 14 can include memory which can be part of, and/or or operatively coupled to, remote system "RS."

Reference may be made to U.S. Patent Publication No. 2012/0116416, filed on Nov. 3, 2011, entitled "Medical Workstation," the entire content of which is incorporated herein by reference, for a detailed discussion of the construction and operation of components of robotic surgical system 1.

Referring now to FIGS. 2-11, surgical assembly 100 includes a guide tube 110, a first surgical instrument 200, a second surgical instrument 300, and one or more surgical portals 400. First and second surgical instruments 200, 300 can be the same and/or different types of instruments (e.g., a grasper, stapler, cutter, sealer, or the like). In some embodiments, surgical assembly 100 includes a second surgical portal 500 and a further second surgical instrument 600 such as an endoscope, for example.

Guide tube 110 extends between a proximal or trailing end 110a of guide tube 100 and a distal or leading end 110b of guide tube 110. A housing 112 is disposed at trailing end 110a of guide tube 110, and an elongated tubular body 114 extends distally from housing 112 to distal end 110b of guide tube 110. Guide tube 110 can be formed from any suitable material such as stainless steel for example to enable sterilization and reuse of guide tube 110. Additionally, and or alternatively guide tube 110 or portions thereof can be formed of transparent material. For example, leading end 110b can be transparent to provide visualization for determining a location/position of surgical instruments advanced therethrough. Guide tube 110 can also be grounded (e.g., via a grounding rod or the like not shown) during electrosurgery, for example, to provide electrical isolation. Guide tube 110 may be electrically configured to detect faulty insulation of an electrosurgery instrument.

Housing 112 includes an outer surface 112a and an inner surface 112b. Housing 112 includes a top surface 112c and a bottom surface 112d. Top surface 112c can form an annular flange 112e that extends radially outwardly from housing 112, and bottom surface 112d can form an annular shoulder 112f that couples elongated tubular body 114 to housing 112.

Elongated tubular body 114 includes an outer surface 114a and an inner surface 114b. Inner surface 114b of elongated tubular body 114 and inner surface 112b of housing 112 define a passage 116 that opens through leading and trailing ends 110a, 110b of guide tube 110.

An internal seal 118, such as a disc seal and/or duckbill valve, for example, is supported in housing 112 and extends from inner surface 112b of housing 112. Internal seal 118 is positioned within housing 112 to receive first and/or second surgical instruments 200, 300 therethrough in a sealed relationship with a respective one of the first and/or second surgical instruments 200, 300.

Each of surgical instruments 200, 300 includes an instrument drive unit 202 supported at a proximal end thereof and a shaft assembly 204 that extends distally from instrument drive unit 202. Shaft assembly 204 includes one or more cables such as cables 206, 208 that extend therealong and/or therethrough to an end effector 210 and/or an end effector 310 coupled to a distal end of shaft assembly 204. For example, end effectors 210, 310 can include any suitable end effector known in the art such as a grasper, stapler, sealer or the like that functions to manipulate, fasten, cut, and/or seal tissue. Proximal ends of cables 206, 208 are coupled to instrument drive unit 202 and actuatable in response to activation of one or more motors 202a supported within instrument drive unit 202 to operate end effectors 210, 310.

Surgical portals 400, 500 are substantially identical and thus in the interest of brevity, only surgical portal 400 is described in detail herein. As shown in FIG. 2, surgical portal 200 includes a body 410 having an outer surface 410a and an inner surface 410b. Inner surface 410b defines a passage 412 that opens at trailing and leading ends 410c, 410d of body 410. Body 410 includes an annular flange 414 that extends radially outwardly from body 410 at trailing end 410c of body 410. An internal seal 416, such as a disc seal and/or a duck-bill valve, for example, is supported in passage 412 that functions to establish a sealed relationship with instruments such as first and second instruments 200, 300 and/or endoscope 600 advanced therethrough into a surgical site "S" while body 410 is positioned within a tract of tissue "T."

In use, as illustrated in FIGS. 2-11, for example, during a laparoscopic procedure, in which an abdominal region of a patient is insufflated to create a working space at the surgical site "S" (although the presently described surgical system can be used in any suitable open or minimally invasive procedure), surgical portals 400, 500 are positioned within tissue "T." As shown in FIG. 2, with endoscope 600 advanced through surgical portal 500 into surgical site "S" adjacent to surgical portal 400, endoscope 600 functions to establish a field of view "F" within surgical site "S" to view surgical site "S," first instrument 200, second instrument 300, guide tube 110, and/or surgical portal 400.

Figure 3:
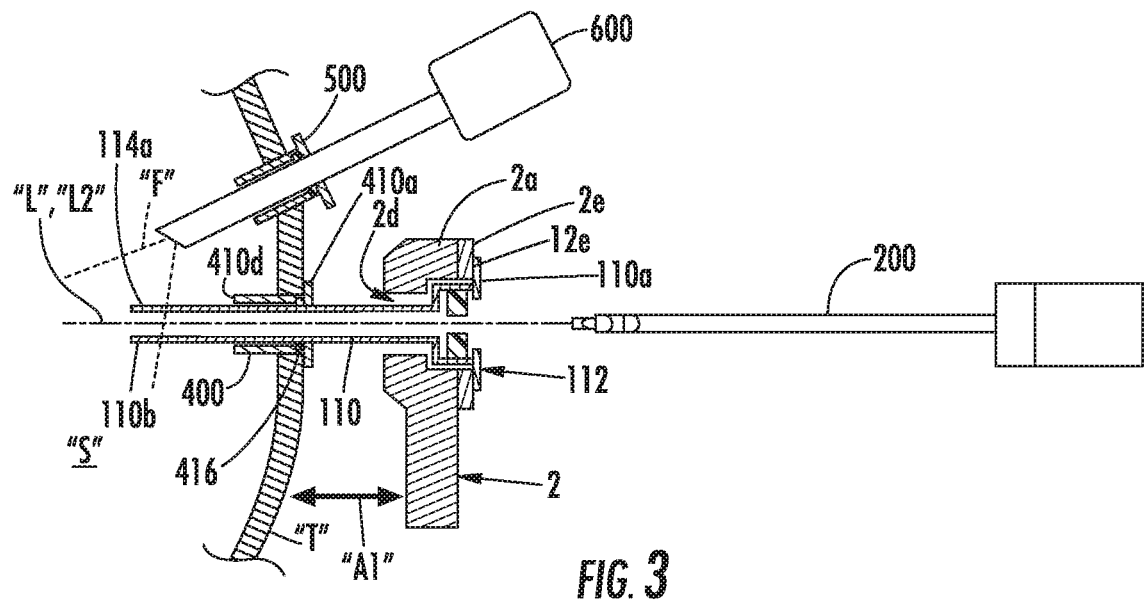
FIGS. 3-11 are progressive views illustrating an instrument exchange procedure conducted in connection with the surgical assembly of FIG. 2.

Referring to FIG. 3, mounting portion 2a of robotic arm 2 is positioned adjacent to, and in alignment with, surgical portal 400 to establish/set a remote center of motion (RCM), for example, a set software-based RCM, based upon the location of surgical portal 400. The location of surgical portal 400 can be stored (e.g., electronically via controller) as desired. The RCM and/or location of robotic arm 2 can be based on a longitudinal axis "L" that extends through leading and trailing ends 410c, 410d of surgical portal 400. Mounting portion 2a of robotic arm 2 may be positioned relative to surgical portal 400 such that a longitudinal axis "L2" that extends through receiving passage 2d of robotic arm 2 is coaxial with longitudinal axis "L" of surgical portal 400. Positioning of robotic arm 2 may be based on electrical communications from control device 4 corresponding to the location of surgical portal 400 and/or longitudinal axis "L" thereof.

Elongated tubular body 114 of guide tube 110 is then advanced through receiving passage 2d of robotic arm 2 such that mounting portion 2a and sterile drape 2e support housing 112 on robotic arm 2 and leading end 110b of guide tube 110 extends into passage 412 of surgical portal 400 with internal seal 416 of surgical portal 400 sealingly engaged with outer surface 114a of guide tube 110. Housing 112 of guide tube 110 can be received in receiving passage 2d of robotic arm 2 such that annular flange 112e of housing 112 engages sterile drape 2e to provide a sterile connection between guide tube 110 and robotic arm 2.

With guide tube 110 supported by robotic arm 2, guide tube 110 can be positioned relative to surgical portal 400 such that leading end 110b of guide tube 110 can extend distally beyond leading end 410d of surgical portal 400 and into surgical site "S." Robotic arm 2 can be moved axially relative to longitudinal axes "L" and "L2," as indicated by arrow "A1," (FIG. 3) to adjust axial positioning of guide tube 110 relative surgical portal 400 while maintaining alignment between robotic arm 2 and surgical portal 400 via guide tube 110. For example, axial movement of guide tube 110 may be effectuated at any time during a procedure to provide access to different areas within surgical site "S" based upon a location of leading end 110b of guide tube 110.

Figure 4:
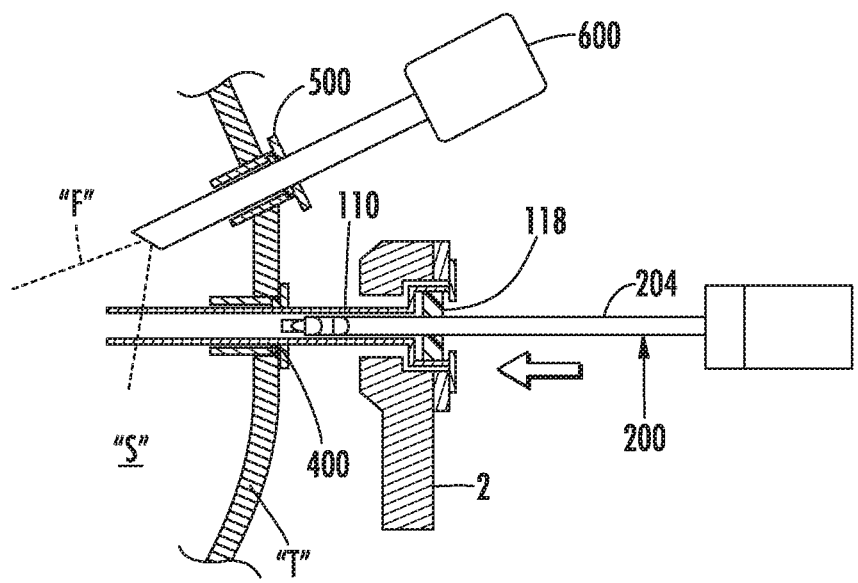
Figure 5:
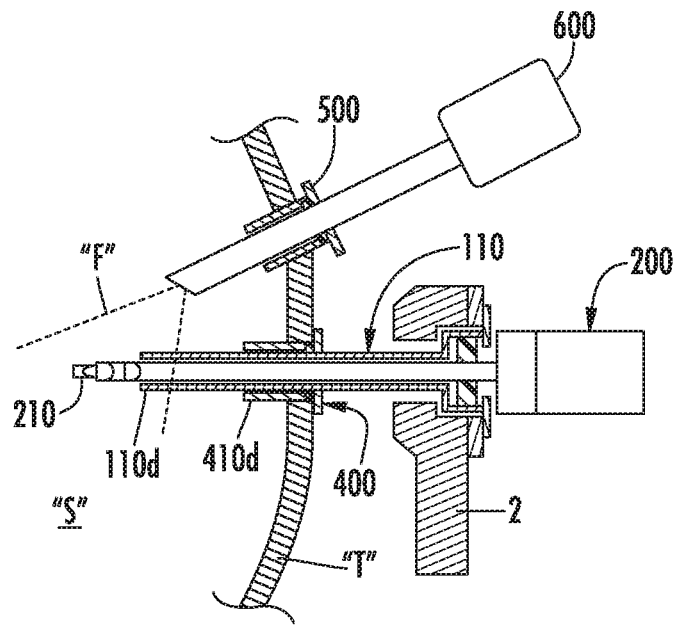
Figure 6:
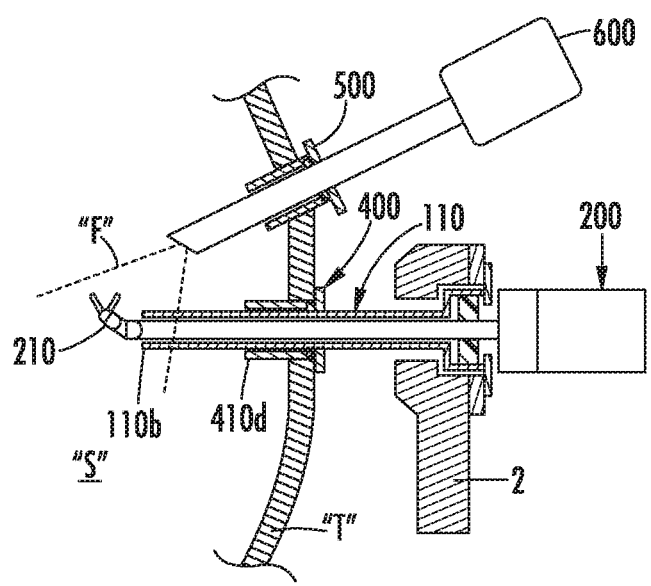
Figure 7:
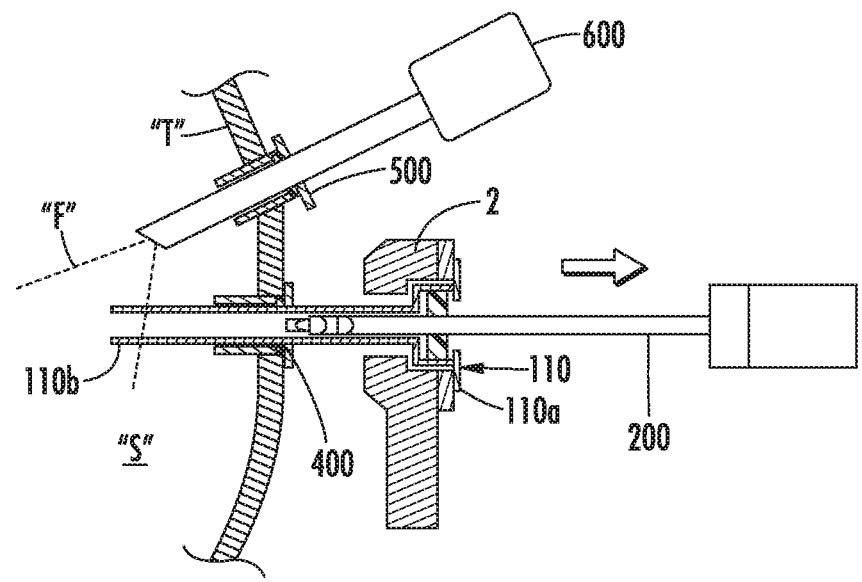
Figure 8:
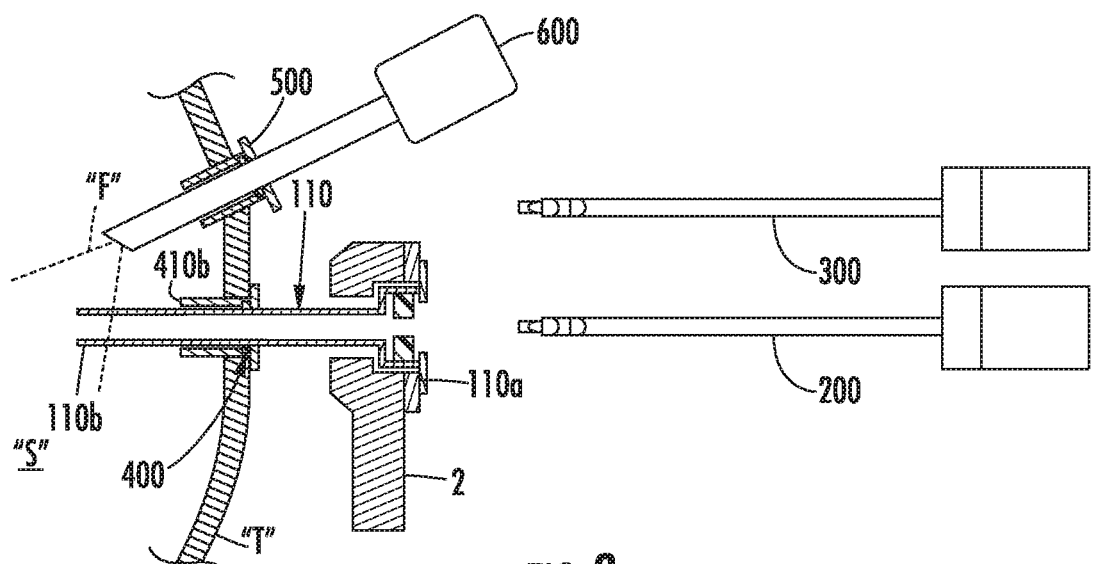
Figure 9:
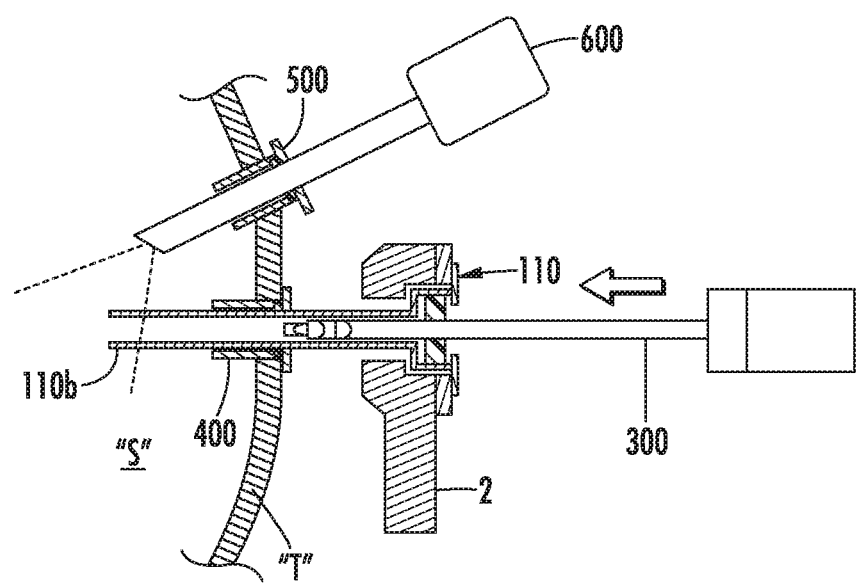
Figure 10:
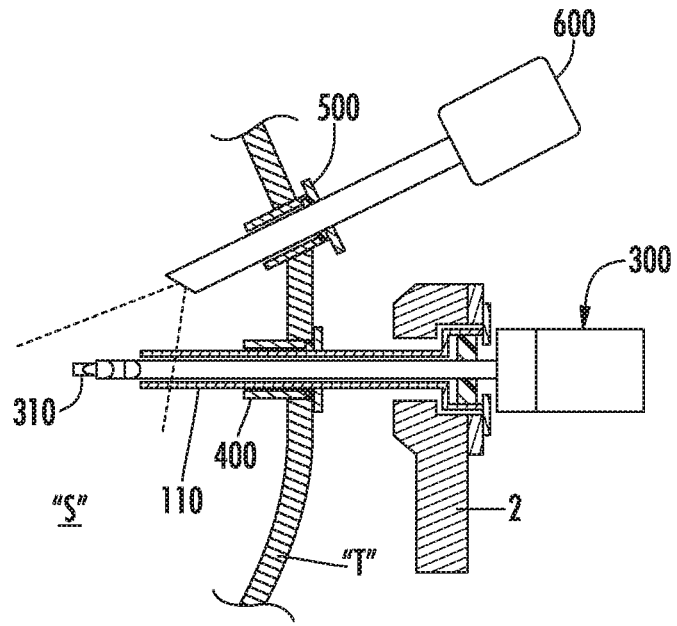
Figure 11:
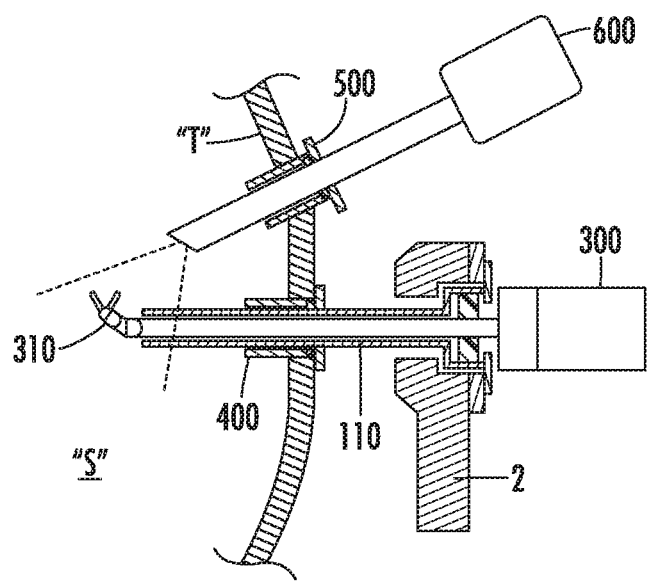

Referring to FIGS. 4-6, guide tube 110 receives, for example, first surgical instrument 200 and establishes a sealed relationship with shaft 204 of first surgical instrument 200 via internal seal 118 as first surgical instrument 200 is received by guide tube 110. First surgical instrument 200 is advanced through guide tube 110 so that end effector 210 of first surgical instrument 200 extends distally beyond leading ends 110b, 410d of guide tube 110 and surgical portal 400, respectively, and into field of view "F" of endoscope 600 within surgical site "S." End effector 210 can then be utilized to operate within surgical site "S" as desired.

With reference to FIGS. 7-11, should a clinician determine that an instrument exchange is required, first surgical instrument 200 can be withdrawn and replaced with second surgical instrument 300. To facilitate effectiveness of the instrument exchange, alignment between robotic arm 2 and surgical portal 400 can be maintained with guide tube 110 (via the software-based RCM) during the entirety of the instrument exchange and including when no surgical instrument is positioned within surgical portal 400. Leading end 110b of guide tube 110 remains within the field of view "F" of endoscope 600 during the procedure and during instrument exchange to enable clinician to determine a final, exact in vivo location of end effector 310 of second surgical instrument 300. One or more subsequent instrument exchanges can be effectuated as desired, similar to that described above, with first surgical instrument 200, second surgical instrument 300, and/or other suitable surgical instruments in order effectuate various steps/procedures with the various instruments. As any of these surgical instruments are advanced in and/or out of guide tube 110, guide tube 110 provides a barricaded conduit to protect surrounding patient tissue from undesired tissue damage resulting from snagging or the like.

It is also contemplated that guide tube 110 can be utilized without surgical portal 400 such that guide tube 110 advances directly through the tissue "T." In embodiments, guide tube 110 includes one or more markings, light emitting diodes, and/or light pipes for various identification purposes. For example, light communicated from a diode or light pipe may communicate information such as whether or not a robotic arm is active, an instrument exchange is being undergone, an instrument is armed, etc. Guide tube 110 may also include one or more sensors for measuring force such as force exerted by tissue (e.g., abdominal wall) which can be subtracted from measured forces applied to a proximal end of one of the instruments.

To improve safety of removing and inserting endoscope 600, guide tube 110 can also be utilized in conjunction with surgical portal 500 to facilitate use of one or more endoscopes 600 in a manner similar to that described with respect to surgical portal 400 and instruments 200, 300. In one embodiment, guide tube 110 may define a separate lumen that receives a fluid (e.g. saline) for cleaning a lens of endoscope 600.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed:

1. A robotic surgical system, comprising:
    a robotic arm;
    a surgical instrument selectively coupled to the robotic arm;
    a surgical portal;
    a controller configured to establish a software-based remote center of motion of the surgical instrument based on a location of the surgical portal when the surgical instrument is inserted in the surgical portal; and
    a guide tube supported by the robotic arm and including an elongated tubular body positioned to receive the surgical instrument, the guide tube insertable in the surgical portal to maintain alignment between the robotic arm and the surgical portal.

2. The robotic surgical system of claim 1, wherein the guide tube is slidably movable relative to the surgical portal in response to movement of the robotic arm.

3. The robotic surgical system of claim 2, wherein the guide tube defines a first longitudinal axis and the surgical portal defines a second longitudinal axis, the first longitudinal axis configured to maintain coaxial alignment with the second longitudinal axis during a surgical instrument exchange.

4. The robotic surgical system of claim 1, wherein the guide tube includes an internal seal configured to maintain a sealed relationship with the surgical instrument when the surgical instrument is received within the elongated tubular body of the guide tube.

5. The robotic surgical system of claim 1, wherein the guide tube includes an electrically conductive material.

6. The robotic surgical system of claim 1, further including a sterile drape positioned between the guide tube and the robotic arm.

7. A method of robotic surgery, comprising:
    setting a software-based remote center of motion (RCM) of a robotic arm when a guide tube supported by the robotic arm is inserted in a surgical portal;
    robotically moving the robotic arm and a surgical instrument about the set software-based RCM; and
    maintaining an alignment between the robotic arm and the surgical portal during a surgical instrument exchange.

8. The method of claim 7, wherein setting the software-based RCM includes storing a location of the surgical portal.

9. The method of claim 8, further including electrically communicating a location of the surgical portal to the robotic arm.

10. The method of claim 7, wherein robotically moving the robotic arm and the surgical instrument about the set software-based RCM includes sliding the guide tube relative to the surgical portal.

11. The method of claim 7, further including advancing an endoscope through a second surgical portal adjacent to the surgical portal, and positioning the endoscope to maintain the guide tube within a field of view of the endoscope.

12. The method of claim 11, further including maintaining the guide tube within the field of view of the endoscope during the surgical instrument exchange.

13. A robotic surgical system, comprising:
   a robotic arm;
   a surgical instrument;
   a surgical portal;
   a controller configured to establish a software-based remote center of motion of the surgical instrument based on a location of the surgical portal; and
   a guide tube supported by the robotic arm and positioned to receive the surgical instrument, the guide tube positionable in the surgical portal to maintain alignment between the robotic arm and the surgical portal.

14. The robotic surgical system of claim 13, wherein the guide tube is slidably movable relative to the surgical portal in response to movement of the robotic arm.

15. The robotic surgical system of claim 14, wherein the guide tube defines a first longitudinal axis and the surgical portal defines a second longitudinal axis, the first longitudinal axis configured to maintain coaxial alignment with the second longitudinal axis during a surgical instrument exchange.

16. The robotic surgical system of claim 13, wherein the guide tube includes an internal seal configured to maintain a sealed relationship with the surgical instrument when the surgical instrument is received within an elongated tubular body of the guide tube.

17. The robotic surgical system of claim 13, wherein the guide tube includes an electrically conductive material.

18. The robotic surgical system of claim 13, further including a sterile drape positioned between the guide tube and the robotic arm.

19. The robotic surgical system of claim 13, wherein the surgical instrument is selectively coupled to the robotic arm.

20. The robotic surgical system of claim 13, further comprising an endoscope and a second surgical portal positioned to receive the endoscope to enable the endoscope to maintain the guide tube within a field of view of the endoscope when the guide tube is inserted within a patient.

* * * * *